(12) United States Patent
Amon

(10) Patent No.: US 11,357,961 B2
(45) Date of Patent: Jun. 14, 2022

(54) CONNECTOR FOR CONNECTING A CATHETER TO A FLUID TRANSFER SYSTEM

(71) Applicant: Fresenius Kabi Deutschland GmbH, Bad Homburg (DE)

(72) Inventor: Barbara Amon, Idstein (DE)

(73) Assignee: Fresenius Kabl Deutschland GmbH, Bad Homburg (DE)

( * ) Notice: Subject to any disclaimer, the term of this patent is extended or adjusted under 35 U.S.C. 154(b) by 105 days.

(21) Appl. No.: 16/099,811

(22) PCT Filed: Apr. 21, 2017

(86) PCT No.: PCT/EP2017/059500
§ 371 (c)(1),
(2) Date: Nov. 8, 2018

(87) PCT Pub. No.: WO2017/207166
PCT Pub. Date: Dec. 7, 2017

(65) Prior Publication Data
US 2019/0111244 A1    Apr. 18, 2019

(30) Foreign Application Priority Data
May 30, 2016 (EP) .................... 16171897

(51) Int. Cl.
*A61M 39/10* (2006.01)
*A61M 39/12* (2006.01)
(52) U.S. Cl.
CPC .... *A61M 39/1011* (2013.01); *A61M 39/1055* (2013.01); *A61M 39/12* (2013.01)

(58) Field of Classification Search
CPC .......... A61M 39/1011; A61M 39/1055; A61M 39/10; A61M 39/12; A61M 2039/1061; A61M 2039/1033; A61M 2039/1066
See application file for complete search history.

(56) References Cited

U.S. PATENT DOCUMENTS

| 5,827,230 A | 10/1998 | Bierman et al. |
| 6,099,519 A * | 8/2000 | Olsen ................ A61M 16/0463 604/171 |

(Continued)

FOREIGN PATENT DOCUMENTS

| DE | 1210277 B | 2/1966 |
| DE | 1210277 B | 2/1966 |

(Continued)

OTHER PUBLICATIONS

International Search Report and Written Opinion, counterpart International Appl. No. PCT/EP2017/059500 dated Aug. 16, 2017 (16 pages).

(Continued)

*Primary Examiner* — Kevin C Sirmons
*Assistant Examiner* — Alexandra Lalonde
(74) *Attorney, Agent, or Firm* — Cook Alex Ltd.

(57) ABSTRACT

The invention relates to a connector (1) for connecting a catheter (2) to a fluid transfer system comprising a main body (11) with a tubular pin (111) adapted to be inserted into an end portion (21) of the catheter (2) such as to provide a fluid connection between the catheter (2) and the tubular pin (111). The connector (1) is characterized in that a fixing means (12) is movably connected to the main body (11), wherein the fixing means (11) is adapted to fix the catheter (2) to the connector (1) when the fixing means (12) is in a fixing position.

7 Claims, 4 Drawing Sheets

(56) References Cited

U.S. PATENT DOCUMENTS

Figure 1:
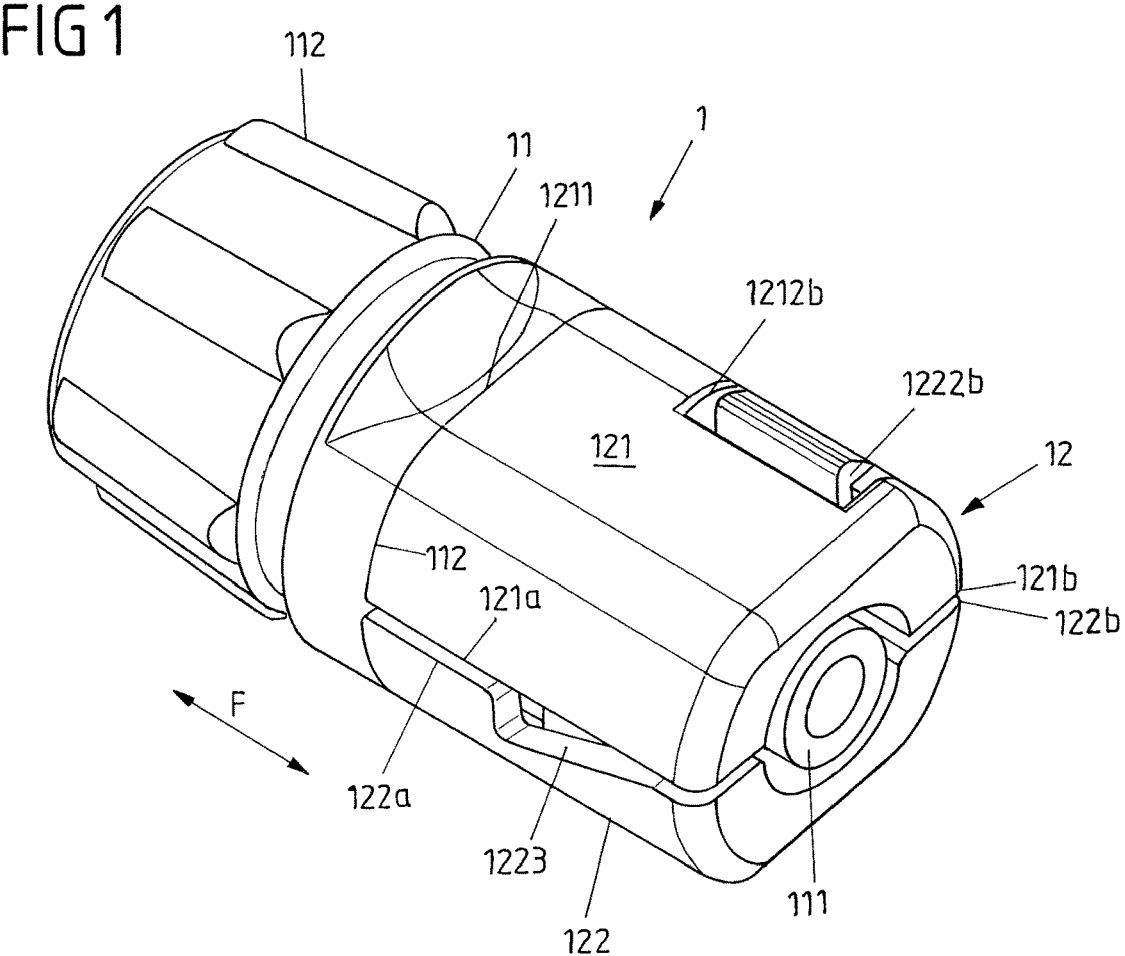

| | | | |
|---|---|---|---|
| 6,155,610 A * | 12/2000 | Godeau | F16L 25/0045 |
| | | | 285/242 |
| 10,203,058 B2 | 2/2019 | Lewis et al. | |
| 2005/0209581 A1* | 9/2005 | Butts | A61M 25/0097 |
| | | | 604/523 |
| 2005/0253390 A1* | 11/2005 | Blazek | F16L 37/0847 |
| | | | 285/420 |
| 2009/0179422 A1* | 7/2009 | Werth | F16L 33/2071 |
| | | | 285/243 |
| 2013/0060268 A1* | 3/2013 | Herrig | A61M 39/1011 |
| | | | 606/153 |
| 2015/0308598 A1 | 10/2015 | Lewis et al. | |

FOREIGN PATENT DOCUMENTS

| | | | | |
|---|---|---|---|---|
| DE | 689 07 128 T2 | 9/1993 | | |
| DE | 10 2005 043 535 A1 | 3/2007 | | |
| EP | 0343910 B1 | 11/1989 | | |
| EP | 3332834 A1 * | 6/2018 | | A61M 39/1011 |
| WO | WO2014/177298 A1 | 11/2014 | | |

OTHER PUBLICATIONS

First Office Action with English translation, counterpart Chinese App. No. 201780033050.1 (dated Nov. 4, 2020) (13 pages).

* cited by examiner

CONNECTOR FOR CONNECTING A CATHETER TO A FLUID TRANSFER SYSTEM

CROSS-REFERENCE TO RELATED APPLICATIONS

This application is a 371 of PCT/EP2017/059500, filed on Apr. 21, 2017, which claims priority to European Patent Application No. 16171897.8, filed on May 30, 2016.

The invention relates to a connector for connecting a catheter to a fluid transfer system according to claim 1.

For administering a fluid (such as a pharmaceutical preparation, irrigation solution or enteral nutrition and hydration) to a patient in intravenous, neuraxial, enteral or other therapies a catheter (with its distal end) is introduced into the patient and connected to a fluid transfer system that provides the fluid to be administered (with its proximal end). The proximal catheter end is connected to the fluid transfer system via a connector system.

From the state of the art a connector system is known that comprises three separate elements. The connector system comprises a nut that is to be slid over the catheter and a main body that is to be introduced partially into the catheter. The nut and the main body may be screwed together to hold the catheter. In order to ensure that the nut and the main body are correctly screwed together a third element (a screw aid) may be used. After the nut has been correctly secured to the main body, the screw aid is usually removed from connector. Such a connector system may be difficult to handle.

It is an object of the present invention to provide a connector for connecting a catheter to a fluid transfer system that is easy to handle and allows securing the catheter reliably.

To solve this problem the connector of claim 1 is provided. This connector comprises a main body with a tubular pin adapted to be inserted into an end portion of a catheter such as to provide a fluid connection between the catheter and the tubular pin. The end portion may be a proximal end portion. The tubular pin may be in fluid connection with a conduit of the main body. While the tubular pin forms the connection site for the catheter, a further connection site for connecting the fluid transfer system may be provided. This connection site may be an ENFIT connector according to ISO 80369, for example part 3 (for enteral devices) or part 6 (for neuraxial devices). The connection site of the fluid transfer system may be in fluid connection with the conduit of the main body, so that that the tubular pin is in fluid connection with the connection site of the fluid transfer system. A fluid may flow from the connection site of the fluid transfer system to the tubular pin (or vice versa) along a fluid flow direction. The tubular pin may extend along the fluid flow direction.

The connector further comprises a fixing means that is movably connected to the main body. The fixing means is adapted to fix the (proximal) end of the catheter to the connector when the fixing means is in a fixing position and when the tubular pin is inserted into the end portion of the catheter. Such a connector is easy to handle as only a single element is required to fix the catheter to the connector.

According to an aspect, the fixing means in the fixing position may be adapted to clamp the end portion of the catheter between the tubular pin and the fixing means, wherein the clamping force acts substantially transverse to the fluid flow direction. Therefore, the distance between the fixing means and the tubular pin (transverse to the fluid flow direction)—when the fixing position of the fixing means is adopted—may at least partially be smaller than the material thickness of the catheter.

According to a further aspect, the fixing means in the fixing position encloses the tubular pin substantially along its entire circumference (the circumference being considered as extending perpendicularly to the fluid flow direction). This means that the fixing means may have a sleeve-like shape and may be arranged along the fluid flow direction substantially coaxially with the tubular pin such that the fixing means extends in a distance around the tubular pin when the fixing means is in the fixing position.

According to an aspect, the fixing means may comprise at least one fixing element that is swiveling mounted to the main body. The at least one fixing element may be swiveling between the fixing position and a plurality of non-fixing positions. The at least one fixing element may be connected to the main body via a hinge.

In case that the fixing means comprises exactly one fixing element, the fixing element may be made of a flexible material such that the shape of the fixing element may be sleeve-like in the fixing position and different (for example a strip, an arc) in any of the non-fixing positions. When moving the fixing element from a non-fixing position into the fixing position, the shape of the fixing element may be deformed by a practitioner to adopt the sleeve-like shape when the fixing position is reached.

According to an aspect, the fixing means comprises a first fixing element and a second fixing element that are each independently swiveling mounted to the main body. The first and second fixing elements may be designed and shaped such that in the fixing position they substantially entirely enclose the tubular pin along its circumference (the circumference being considered as extending perpendicularly to the fluid flow direction). For example, the first and second fixing elements may be designed and shaped such that in the fixing position each fixing element encloses the tubular pin along its circumference by substantially 180°. For instance, the first and second fixing elements may have a substantially arc shaped cross section (in a plane perpendicular to the fluid flow direction). The first fixing element and the second fixing element may be mounted at two different positions to the main body. For instance, the first fixing element and the second fixing element may be mounted to the main body at two diametrically opposed positions with respect to the tubular pin. This allows to move both fixing elements simultaneously into the fixing position using only one hand. When moving the first and second fixing elements from a non-fixing-position into the fixing position the first and second fixing elements here move towards the tubular pin and towards each other.

According to an aspect, the first fixing element and the second fixing element may each comprise at least one connecting element. The at least one connecting element of the first fixing element may be adapted and provided to cooperate with the at least one connecting element of the second fixing element (and vice versa) such as to maintain the fixing means in the fixing position. For instance, the first fixing element and the second fixing element may each comprise exactly one connecting element forming a pair of connecting elements. Each connecting element may be provided at an end of the first and second fixing element. The ends may be those ends that in the fixing position extend along the tubular pin. For instance, the connecting elements may be arranged at one such end of the first and second fixing elements that face each other in the fixing position such that the connecting elements are connected to each other outside the circumference of the tubular pin (along the fluid flow direction). As an alternative the first fixing element and the second fixing element may each comprise exactly two connecting elements forming two pairs of connecting elements. As each fixing element has two ends that in the fixing position extend along the tubular pin and that are diametrically opposed to each other with respect to the tubular pin, each connecting element may be provided at one such end. In this case the connecting elements are connected to each other at two sites outside the circumference of the tubular pin (along the fluid flow direction). These two sites may be diametrically opposed to each other with respect to the tubular pin. As a further alternative the first fixing element and the second fixing element may each comprise more than two connecting elements. In this case all connecting elements may be provided at only one end of the first and second fixing element, wherein the ends face each other in the fixing position. Alternatively, the connecting elements may be arranged at both ends of the first and second fixing element.

According to an aspect, the at least one connecting element of the first fixing element and the at least one connecting element of the second fixing element may be in non-detachable connection when the fixing means is in the fixing position. That is, once the connection between the at least one connecting element of the first fixing element and the at least one connecting element of the second fixing element has been established it cannot be disconnected accidentally by inverting the movement of the connecting elements for establishing the connection.

A pair of connecting elements may comprise a latching element provided at the first (second) fixing element and a corresponding recess provided at the second (first) fixing element adapted to establish a latching connection.

According to a further aspect, the main body may comprise at least one stop element that is arranged between the first fixing element and the second fixing element when the fixing means is in the fixing position. The at least one stop element may be provided at the main body. The main body may have a surface that extends substantially perpendicular to the fluid flow direction, wherein the tubular pin and the at least one stop element may protrude from this surface of the main body along the fluid flow direction into the same sense (orientation) away from the connection site of the fluid transfer system. The at least one stop element may be shorter than the tubular pin (along the fluid flow direction). In the fixing position, each fixing element may butt against the at least one stop element with one of its ends that in the fixing position face each other and extend along the tubular pin. For instance, two stop elements may be provided such that in the fixing position each fixing element may butt against each stop element with one of its ends that in the fixing position extends along the tubular pin. The two stop elements may be arranged diametrically opposed to each other with respect to the tubular pin. The stop element(s) may prevent a rotational movement of the first and second fixing elements when the fixing position is adopted and thus protect the connection between the main body and the fixing elements (the hinges) against shear stress.

According to an aspect, the at least one fixing means may comprise at least one salient arranged on an inner surface of the at least one fixing means such that in the fixing position the end portion of the catheter is clamped between the at least one salient and the tubular pin. The inner surface of the at least one fixing means is the surface that is oriented towards the tubular pin when the fixing means is in the fixing position. The at least one salient may protrude from the surface towards the tubular pin. For instance each fixing element may comprise at least one such salient. The at least one salient may extend over the entire circumference of each fixing element. Alternatively, the at least one salient may be shorter than the entire circumference of each fixing element. In this case a plurality of salients may be arranged in a row extending along the circumference of a fixing element.

A plurality of such salients may be provided at each fixing element along the fluid flow direction. In this case the size of the salients (that is their extension along the fluid flow direction and their thickness) may be the same or different. The thickness is defined as the extension of a salient perpendicular to the inner surface. For instance, their thickness may increase successively while their extension along the fluid flow direction remains substantially constant. For the sake of stability, both their thickness and their extension along the fluid flow direction may increase successively. For instance the evolution of the thickness may correlate with the evolution of the external diameter of the tubular pin. The thickness of the salients may for example evolve indirectly proportional to the external diameter of the tubular pin.

According to an aspect, the tubular pin may have a free first end and a second end at which the tubular pin is attached to the main body. The outer diameter of the tubular pin may increase from the first end to the second end of the tubular pin. This allows to use catheters of different diameter with one type of connector. Catheters with a greater diameter may be pulled over a longer section of the tubular pin than catheters with a smaller diameter. The outer diameter may increase continuously, for instance conically. Alternatively the outer surface of the tubular pin may have a saw tooth profile, wherein the outer diameter increases within one saw tooth from the first end to the second end of the tubular pin. Furthermore, the size of successive saw teeth may increase from the first end to the second end of the tubular pin such that the outer diameter of successive teeth increases from the first end to the second end of the tubular pin.

According to an aspect, the fixing means in the fixing position may extend over the entire length (from the first end to the second end) of the tubular pin. This allows to apply clamping force to the catheter over a maximum length and thus to hold the catheter securely in the connector.

According to an aspect, the connector may be made in one piece. For instance the connector may be made of a plastic material. The connector may be produced in a plastic injection moulding process.

Figure 2:
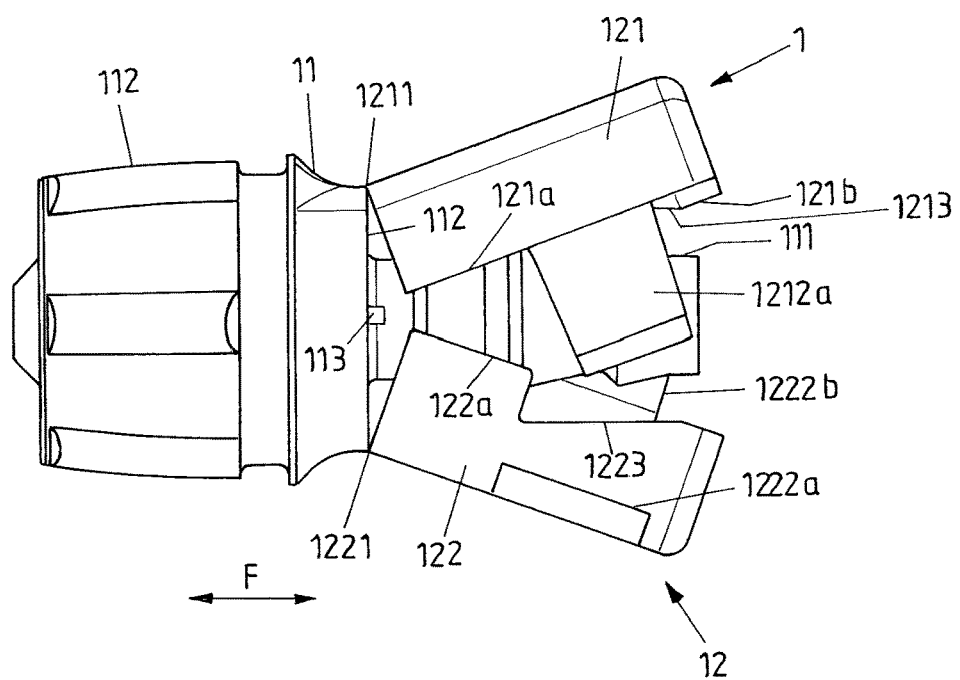
Figure 3:
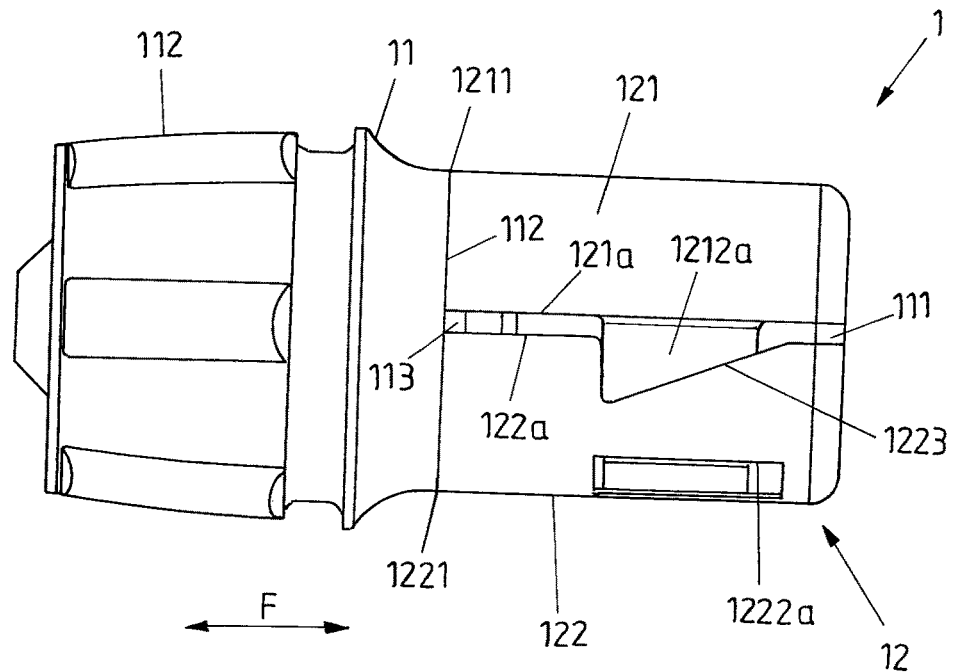
Figure 4:
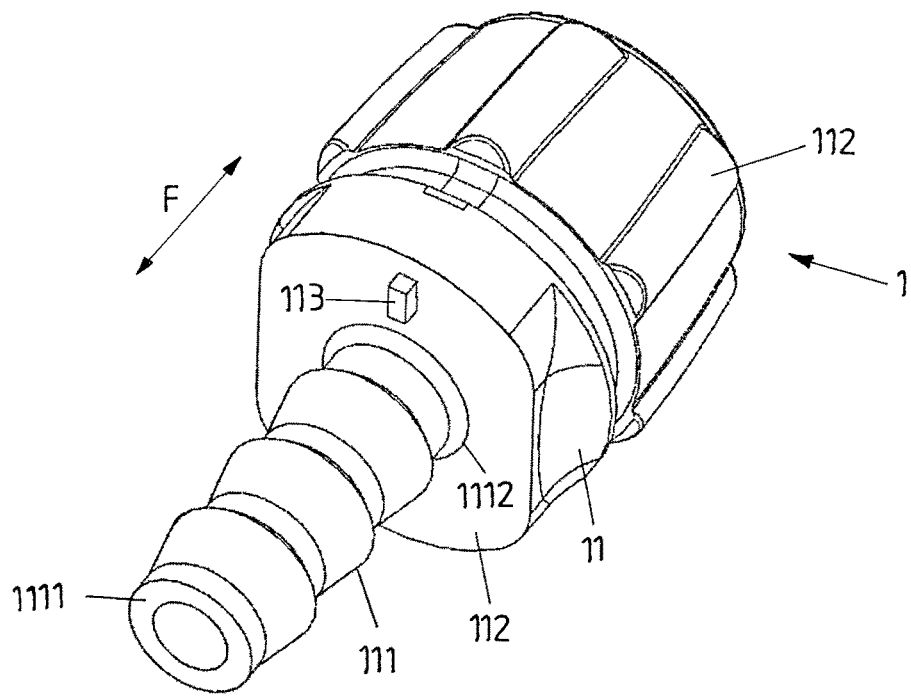
Figure 6:
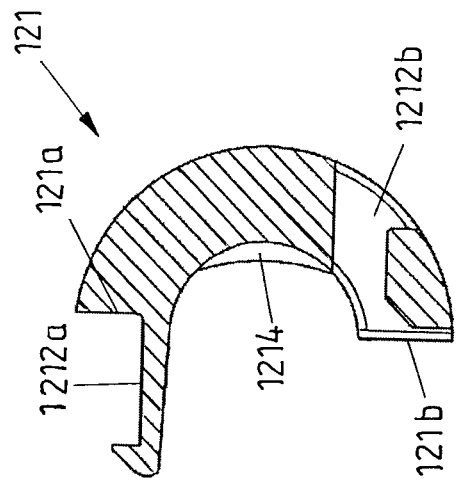
Figure 5:
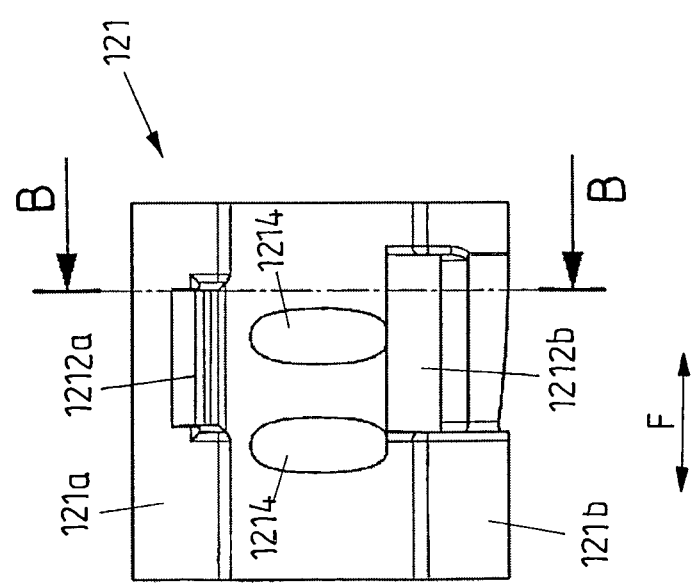
Figure 7:
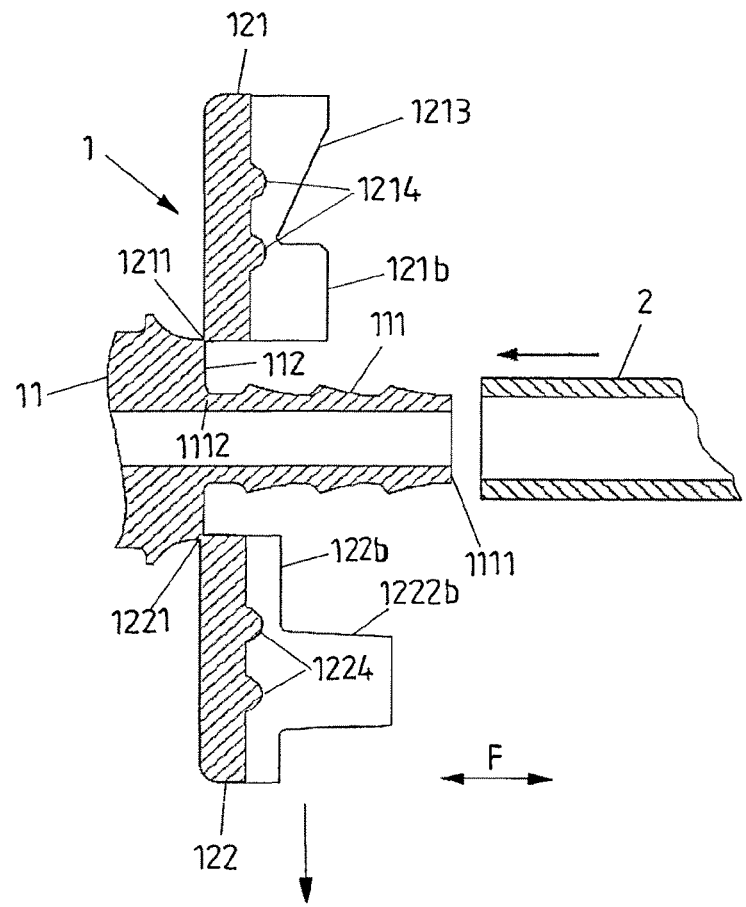
Figure 8:
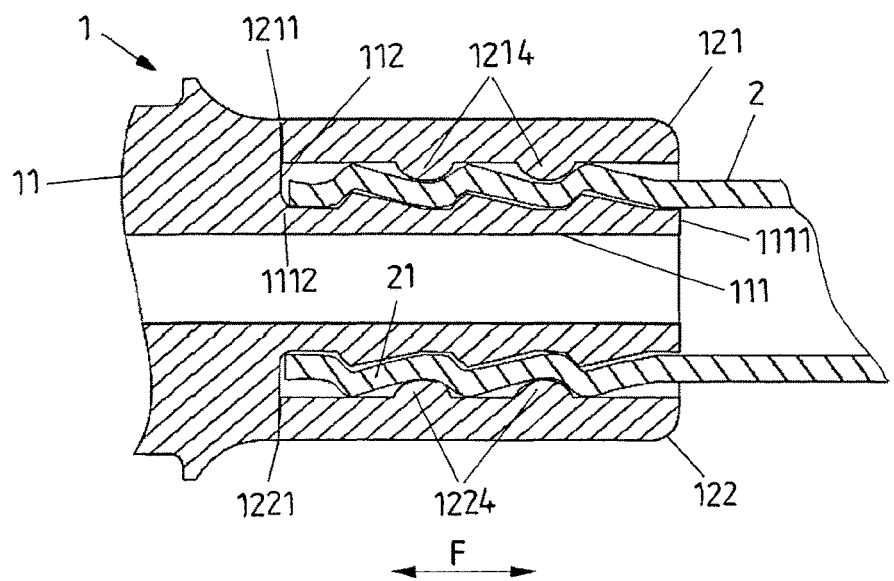

The idea underlying the invention is shown in the figures. The parts in the figures are not necessarily to scale, instead emphasis being placed upon illustrating principles of the invention. Moreover, in the figures, like reference numerals designate corresponding parts. In the drawings:

FIG. 1 schematically shows a perspective view of a connector with a fixing means being in the fixing position according to an embodiment;

FIG. 2 schematically shows a side view of a connector with a fixing means being in a non-fixing position according to another embodiment;

FIG. 3 schematically shows a side view of the connector of FIG. 2 with the fixing means being in the fixing position;

FIG. 4 schematically shows a perspective view of a main body and a tubular pin of the connector of FIGS. 1 and 2 according to an embodiment;

FIG. 5 schematically shows an inner surface of a fixing element of the connector of FIG. 2 according to an embodiment;

FIG. 6 schematically shows a cross section through the fixing element of FIG. 5 along line B-B;

FIG. 7 schematically shows a cross section through the connector of FIG. 1 with the fixing means being in a non-fixing position and an unconnected catheter; and FIG. 8 schematically shows a cross section through the connector of FIG. 7 with the fixing means being in the fixing position and the catheter of FIG. 7 connected to the connector.

In the following detailed description, reference is made to the accompanying drawings which form a part hereof and in which are shown by way of illustration specific embodiments in which the invention may be practiced.

In this regard, it is to be understood that other embodiments may be utilized and structural or logical changes may be made without departing from the scope of the present invention. The following detailed description, therefore, is not to be taken in a limiting sense, and the scope of the present invention is defined by the appended claims.

Reference will now be made in detail to various embodiments, one or more examples of which are illustrated in the figures. Each example is provided by way of explanation, and is not meant as a limitation of the invention. For example, features illustrated or described as part of one embodiment can be used on or in conjunction with other embodiments to yield yet a further embodiment. It is intended that the present invention includes such modifications and variations. The examples are described using specific language which should not be construed as limiting the scope of the appended claims. The drawings are not scaled and are for illustrative purposes only. For clarity, the same elements have been designated by the same references in the different drawings if not stated otherwise.

FIG. 1 shows a connector 1 for connecting a catheter 2 (FIGS. 7 and 8) to a fluid transfer system (not shown) according to an embodiment. The connector 1 comprises a main body 11 with a tubular pin 111. The tubular pin 111 serves as a first connection site for connecting the catheter 2 (with its proximal end) to the connector 1. For connecting the catheter 2 to the tubular pin 111 the catheter 2 is pulled over the tubular pin 111 where it is primarily hold by frictional forces. The connector 1 extends along a longitudinal axis that also defines a fluid flow direction F along which a fluid to be transferred flows from the fluid transfer system through the connector 1 to the catheter 2. The main body 11 comprises a second connection site 112 for connecting the fluid transfer system to the connector 1. In the embodiment of FIG. 1 the second connection site 112 is an ENFIT connector according to ISO 80369. The tubular pin 111 and the second connection site 112 are arranged one after another along the fluid flow direction F. The tubular pin 111 and the second connection site 112 are in fluid connection.

The connector 1 further comprises a fixing means 12 that is movably connected to the main body 11. The fixing means 12 is movable between a plurality of non-fixing positions and a fixing position. In FIG. 1 the fixing means 12 being in the fixing position is shown. In the fixing position the fixing means 12 extends along the entire tubular pin 111 (along the fluid flow direction) on the one hand and substantially along the entire circumference of the tubular pin 111 (perpendicular to the fluid flow direction) on the other hand. In the fixing position the fixing means 12 is adapted to press the catheter 2 against the tubular pin 111 such that the catheter 2 is hold by compression between the fixing means 12 and the tubular pin 111.

The fixing means 12 comprises a first fixing element 121 and a second fixing element 122. Each fixing element 121, 122 is swiveling mounted to the main body 11. In this respect for each fixing element 121, 122 a hinge 1211, 1221 is provided. The hinges 1211, 1221 are arranged diametrically opposed to each other with respect to the tubular pin 111 that extends in between the hinges 1211, 1221. In the fixing position each fixing element 121, 122 encloses the circumference of the tubular pin 111 by substantially 180°. The circumference is considered as extending perpendicularly to the fluid flow direction. The fixing elements 121, 122 have a substantially arc shaped cross section (in a plane perpendicular to the fluid flow direction). Each arc has two ends so that each fixing element 121, 122 has two ends 121a, 121b, 122a, 122b that all extend along the fluid flow direction. In the fixing position the end 121a of the first fixing element 121 faces the end 122a of the second fixing element 122, while the end 121b of the first fixing element 121 faces the end 122b of the second fixing element 122.

Each fixing element 121, 122 comprises one connecting element 1212b, 1222b. The connecting elements 1212b, 1222b are adapted and provided to cooperate with each other such as to maintain the fixing means 12 in the fixing position. The connecting elements 1212b, 1222b are arranged at the end 121b of the first fixing element 121 and at the end 122b of the second fixing element 122, respectively. The connecting elements 1212b, 1222b are arranged such that they are brought into engagement when the fixing means 12 is moved from a non-fixing position into the fixing position. No further action by the user is thus required to establish the connection between the connecting elements 1212b, 1222b. In the embodiment of FIG. 1 the connecting element 1222b of the second fixing element 122 is a latching element and the connecting element 1212b of the first fixing element 121 is a corresponding recess that is adapted to receive the latching element in the fixing position. The latching element and the recess are designed such that they cannot be brought out of engagement accidentally.

At the end 122a of the second fixing element 122 an indentation 1223 is provided. The indentation 1223 allows a practitioner to have a look through the fixing means 12 onto the catheter 2 and the tubular pin 111 in order to verify whether the catheter 2 is correctly positioned on the tubular pin 111. Another indentation is provided at the end 121b of the first fixing element 121.

Further details of the fixing elements 121, 122 and the tubular pin 111 will be described later with reference to FIGS. 4 to 6.

In FIGS. 2 and 3 a further embodiment of the connector 1 is shown. In FIG. 2 the fixing means 12 is in a non-fixing position, while in FIG. 3 the fixing means 12 is in the fixing position. The embodiment of FIGS. 2 and 3 differs from the embodiment of FIG. 1 substantially in that not only one pair of connecting elements (1212b, 1222b at the end 121b of the first fixing element 121 and at the end 122b of the second fixing element 122, respectively) is provided, but two pairs of connecting elements 1212a, 1222a, 1212b, 1222b are provided. The additional pair of connecting elements 1212a, 1222a is provided at the end 121a of the first fixing element 121 and at the end 122a of the second fixing element 122, respectively. When moving the fixing means 12 from a non-fixing position (FIG. 2) into the fixing position (FIG. 3) by moving the first and second fixing elements 121, 122 two connections between the two fixing elements 121, 122 are thus provided simultaneously. In the embodiment of FIGS. 2 and 3 the connecting element 1212a of the first fixing element and the connecting element 1222b of the second fixing element 122 are latching elements, while the connecting element 1212b of the first fixing element 121 and the connecting element 1222a of the second fixing element 122 are corresponding recesses. In the fixing position the latching elements (and the recesses) are thus arranged diametrically opposed to each other with respect to the tubular pin 111. In the fixing position the latching elements project through the recesses where they are securely hold.

FIG. 4 shows the main body 11 (with its tubular pin 111) of the connectors 1 according to the embodiments of FIGS. 1 to 3. The main body 11 has a surface 112 that extends substantially perpendicular to the fluid flow direction F. This surface 112 represents the boundary between the tubular pin 111 on the one hand and the second connection site 112 on the other hand. The tubular pin 111 protrudes from this surface 112 of the main body 11 along the fluid flow direction F. The main body 11 further comprises two stop elements 113 (only one of which is shown in FIG. 4 due to the perspective) that are provided diametrically opposed to each other with respect to the tubular pin 111. The stop elements 113 protrude from the surface 112 of the main body along the fluid flow direction in the same sense as the tubular pin 111. The stop elements 113 are shorter than the tubular pin 111. In the fixing position of the fixing means 12 (see for example FIG. 3) the stop elements 113 are arranged between the two fixing elements 121, 122. In the fixing position, the fixing elements 121, 122 butt with their ends 121a, 122a against the one of the two stop elements 113 and with their ends 121b, 122b against the other of the two stop elements 133.

In FIG. 4 the tubular pin 111 is shown in more detail. The tubular pin 111 is a hollow shaft that extends between a free first end 1111 and a second end 1112 at which the tubular pin 111 is attached to the surface 112 of the main body 11. According to FIG. 4, the tubular pin 111 comprises three segments. The number of segments is just exemplary and may differ from three. The three segments are identical in shape and size, but may also be different from one another. In each segment the outer diameter of the tubular pin 111 increases (continuously, for example conically) in a direction from the first end 1111 towards the second end 1112 of the tubular pin 111. At the end of each segment that is oriented towards the second end 1112 of the tubular pin 111 the outer diameter of the tubular pin 111 decreases abruptly such that the outer surface of the tubular pin 111 has a saw tooth profile. Although in FIG. 4 the outer diameter of the tubular pin 111 evolves in the same manner for each segment, it may be provided that the size (in particular the outer diameter) of successive segments increases from the first end 1111 to the second end 1112 of the tubular pin 111. In an alternative the size (in particular the outer diameter) of the segments may evolve differently. Before (seen from the first end 1111 to the second end 1112 of the tubular pin) each segment a substantially cylindrical section may be provided, wherein the cylindrical section has an outer diameter that is substantially identical to the smallest outer diameter of the subsequent segment.

FIG. 5 shows an inner surface of the first fixing element 121 of the connector of the embodiment of FIGS. 2 and 3. FIG. 6 shows a cross section through this first fixing element 121 along line B-B. The inner surface of a fixing element is that surface of the fixing element that is oriented towards the tubular pin 111 when the fixing means 12 is in the fixing position. On the inner surface two salients 1214 are provided that protrude from the inner surface towards the tubular pin 111 when the fixing means 12 is in the fixing position. Each salient 1214 extends along the inner surface between the ends 121a, 121b in a plane substantially perpendicular to the fluid flow direction F. In FIGS. 5 and 6 the salients 1214 do not extend from the one end 121a to the other end 121b of the first fixing element 121. However, it may be provided that the salients extend over the entire distance between the one end 121a and the other end 121b. According to FIG. 5 the salients are identical. However, the salients may be different with respect to their extension between the ends 121a, 121b (length) and/or their extension perpendicular to the inner surface (thickness) and/or their extension along the fluid flow direction F. The number of salients 1214 in FIG. 5 is just exemplarily. For instance only one or more than two salients may be provided that are (regularly) spread over the entire fixing element along the fluid flow direction.

In FIGS. 5 and 6 the first fixing element 121 of the embodiment of FIGS. 2 and 3 is exemplarily shown. It is understood that also the second fixing element 122 of this embodiment as well as the fixing elements of the embodiment of FIG. 1 may comprise salients.

FIG. 7 shows a cross section through the connector of FIG. 1 with the fixing means 12 being in a non-fixing position and a catheter 2 that is to be connected to the connector 1. In a first step an end portion 21 of the catheter 2 is pulled over the tubular pin 111. In a second step the first and second fixing elements 121, 122 are moved towards the tubular pin 111 by a rotational movement about the hinges 1211, 1221 until the fixing position of the fixing means 12 is reached (FIG. 8). Simultaneously a connection between the connecting element 1212b of the first fixing element 121 and the connecting element 1222b of the second fixing element 122 is established. In the fixing position the catheter 2 is compressed between the salients 1214, 1224 and the tubular pin 111 such that the catheter is securely hold by the connector 1.

As can be seen in FIG. 8 the salients 1214, 1224 are provided along the fluid flow direction F such that they protrude from the fixing elements 121, 122 at the transitions between two successive segments of the tubular pin 111. At a transition between two successive segments of the tubular pin 111 the tubular pin 111 has its (local) minimum outer diameter. The salients 1214, 1224 thus urge the catheter 2 in recesses on the outer surface of the tubular pin 111 at the transition of two subsequent segments. The elasticity of the material of the catheter 2 allows the catheter 2 to adopt the shape of the outer surface of the tubular pin 111. As the catheter 2 thus contacts the tubular pin 111 over a maximum contact area, the frictional force between the catheter 2 and the tubular pin 111 is maximized so that the catheter 2 is securely hold in the connector 1.

The invention claimed is:

1. A connector in combination with a catheter for connecting the catheter to a fluid transfer system, the connector comprising a main body having a surface extending perpendicularly to a fluid flow direction, with a tubular pin protruding along the fluid flow direction from the surface extending perpendicularly to the fluid flow direction, the tubular pin being inserted into an end portion of the catheter such as to provide a fluid connection between the catheter and the tubular pin, a fixing means movably connected to the main body, the fixing means comprising a first fixing element and a second fixing element that are each independently mounted to the main body by a hinge, wherein the hinge for the first fixing element is diametrically opposed to the hinge for the second fixing element, with respect to the tubular pin, wherein the fixing means is adapted to fix the catheter to the connector when the fixing means is in a fixing position by enclosing the tubular pin substantially along an entire circumference of the tubular pin, the tubular pin comprising a plurality of successive segments with a transition between the successive segments defined by a local minimum outer diameter, each of the first and second fixing elements comprising at least one salient arranged on an inner surface of the first fixing element and an inner surface of the second fixing element such that, when in the fixing position, the end portion of the catheter is clamped between the at least one salient on each of the first and second fixing elements and the transition between the successive segments of the tubular pin, the main body further comprising first and second diametrically opposed stop elements protruding in the fluid flow direction from the surface extending perpendicularly to the fluid flow direction of the main body, the stop elements being arranged in a space between the first fixing element and the second fixing element when the fixing means is in the fixing position, the stop elements being configured so that the first and the second fixing elements butt with ends of the first and the second fixing elements against the stop elements, such that the stop elements prevent a rotational movement of the first and second fixing elements when the first and the second fixing elements are in the fixing position.

2. The connector according to claim 1, wherein the fixing means in the fixing position is adapted to clamp the end portion of the catheter between the tubular pin and the fixing means.

3. The connector according to claim 1, wherein the first fixing element and the second fixing element each comprise at least one connecting element, wherein the at least one connecting element of the first fixing element is adapted to cooperate with the at least one connecting element of the second fixing element such as to maintain the fixing means in the fixing position.

4. The connector according to claim 3, wherein the at least one connecting element of the first fixing element and the at least one connecting element of the second fixing element are in non-detachable connection when the fixing means is in the fixing position.

5. The connector according to claim 1, wherein the tubular pin has a free first end and a second end at which the tubular pin is attached to the main body, wherein the tubular pin has an outer diameter that increases from the free first end to the second end of the tubular pin.

6. The connector according to claim 1, wherein the fixing means in the fixing position extends over an entire length of the tubular pin.

7. The connector according to claim 1, wherein the connector is configured to be made in one piece.

* * * * *